(12) United States Patent
Von Arx

(10) Patent No.: US 7,069,086 B2
(45) Date of Patent: Jun. 27, 2006

(54) METHOD AND SYSTEM FOR IMPROVED SPECTRAL EFFICIENCY OF FAR FIELD TELEMETRY IN A MEDICAL DEVICE

(75) Inventor: Jeffrey A. Von Arx, Minneapolis, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 491 days.

(21) Appl. No.: 10/269,905

(22) Filed: Oct. 11, 2002

(65) Prior Publication Data

US 2004/0030260 A1    Feb. 12, 2004

Related U.S. Application Data

(60) Provisional application No. 60/401,966, filed on Aug. 8, 2002.

(51) Int. Cl.
*A61N 1/08* (2006.01)

(52) U.S. Cl. .................... 607/60; 128/903; 607/32
(58) Field of Classification Search ............. None
See application file for complete search history.

(56) References Cited

U.S. PATENT DOCUMENTS

| 4,341,982 A | 7/1982 | Lahti et al. |
| 4,441,498 A | 4/1984 | Nordling ............... 128/419 PG |
| 4,519,401 A | 5/1985 | Ko et al. ............... 118/748 |
| 4,542,532 A | 9/1985 | McQuilkin .............. 455/78 |
| 4,543,954 A | 10/1985 | Cook et al. |
| 4,562,841 A | 1/1986 | Brockway et al. .... 128/419 PG |
| 4,634,294 A | 1/1987 | Christol et al. ............ 374/170 |
| 4,803,987 A | 2/1989 | Calfee et al. ............... 128/419 |
| 4,944,299 A | 7/1990 | Silvian ................. 128/419 PG |
| 4,945,909 A | 8/1990 | Fearnot et al. |
| 5,025,808 A | 6/1991 | Hafner ...................... 600/509 |
| 5,089,019 A | 2/1992 | Grandjean ..................... 623/3 |
| 5,109,853 A | 5/1992 | Taicher et al. ........... 128/653.2 |
| 5,113,869 A | 5/1992 | Nappholz et al. ........... 128/696 |
| 5,314,453 A | 5/1994 | Jeutter ......................... 607/61 |
| 5,342,408 A | 8/1994 | deCoriolis et al. ............ 607/32 |
| 5,350,412 A | 9/1994 | Hoegnelid et al. |
| 5,370,666 A | 12/1994 | Lindberg et al. |

(Continued)

FOREIGN PATENT DOCUMENTS

EP    0168640    1/1986

(Continued)

OTHER PUBLICATIONS

Rawat, Prashant, et al., "Radio Frequency Antenna in a Header of an Implantable Medical Device", U.S. Appl. No. 10/744,943, Filed Dec. 22, 2003, 34 pgs.

*Primary Examiner*—Carl H. Layno
(74) *Attorney, Agent, or Firm*—Schwegman, Lundberg, Woessner & Kluth, P.A.

(57) ABSTRACT

Radio frequency bandwidth from a far field transmitter of an implantable medical device is adjusted by controlling the data rate, the output power level, the transmitter supply voltage or combinations thereof. Adjustments are made on the basis of a sensed temperature, absence or presence of a lead or by way of wave shaping. A Surface Acoustic Wave (SAW) resonator based transmitter exhibits stable bandwidth in a temperature controlled operating environment. For temperatures outside of the range of human body temperature, the output of the SAW-based transmitter is adjusted to provide reduced bandwidth.

52 Claims, 12 Drawing Sheets

U.S. PATENT DOCUMENTS

| | | | | |
|---|---|---|---|---|
| 5,476,488 A | * | 12/1995 | Morgan et al. | 607/30 |
| 5,486,200 A | | 1/1996 | Lindemans | 607/5 |
| 5,516,285 A | | 5/1996 | Yacker et al. | 433/72 |
| 5,535,752 A | | 7/1996 | Halperin et al. | 128/670 |
| 5,579,876 A | | 12/1996 | Adrian et al. | 188/322.17 |
| 5,593,430 A | | 1/1997 | Renger | 607/18 |
| 5,598,847 A | | 2/1997 | Renger | 128/691 |
| 5,650,759 A | | 7/1997 | Hittman et al. | |
| 5,683,432 A | | 11/1997 | Goedeke et al. | |
| 5,697,958 A | | 12/1997 | Paul et al. | |
| 5,752,977 A | | 5/1998 | Grevious et al. | |
| 5,766,232 A | | 6/1998 | Grevious et al. | 607/60 |
| 5,807,397 A | | 9/1998 | Barreras | 607/61 |
| 5,833,603 A | | 11/1998 | Kovacs et al. | 600/317 |
| 5,843,139 A | | 12/1998 | Goedeke et al. | |
| 5,861,019 A | | 1/1999 | Sun et al. | 607/60 |
| 5,904,708 A | | 5/1999 | Goedeke | 607/18 |
| 5,919,210 A | | 7/1999 | Lurie et al. | 607/3 |
| 6,009,350 A | | 12/1999 | Renken | 607/32 |
| 6,093,146 A | | 7/2000 | Filangeri | |
| 6,115,583 A | | 9/2000 | Brummer et al. | 455/41 |
| 6,115,634 A | | 9/2000 | Donders et al. | 607/32 |
| 6,115,636 A | | 9/2000 | Ryan | 607/60 |
| 6,169,925 B1 | | 1/2001 | Villaseca et al. | 607/60 |
| 6,240,317 B1 | | 5/2001 | Villaseca et al. | 607/60 |
| 6,263,246 B1 | | 7/2001 | Goedeke et al. | 607/60 |
| 6,275,737 B1 | | 8/2001 | Mann | |
| 6,309,350 B1 | | 10/2001 | VanTassel et al. | 600/300 |
| 6,329,920 B1 | | 12/2001 | Morrison et al. | |
| 6,388,628 B1 | | 5/2002 | Dettloff et al. | 343/742 |
| 6,424,867 B1 | | 7/2002 | Snell et al. | |
| 6,427,088 B1 | | 7/2002 | Bowman et al. | 607/60 |
| 6,434,429 B1 | | 8/2002 | Kraus et al. | 607/60 |
| 6,443,891 B1 | | 9/2002 | Grevious | |
| 6,456,256 B1 | | 9/2002 | Amundson et al. | 343/873 |
| 6,470,215 B1 | | 10/2002 | Kraus et al. | 607/60 |
| 6,531,982 B1 | | 3/2003 | White et al. | |
| 6,564,104 B1 | | 5/2003 | Nelson et al. | |
| 6,564,105 B1 | | 5/2003 | Starkweather et al. | |
| 6,574,509 B1 | | 6/2003 | Kraus et al. | 607/60 |
| 6,574,510 B1 | | 6/2003 | Von Arx et al. | |
| 6,577,900 B1 | * | 6/2003 | Silvian | 607/60 |
| 6,577,901 B1 | | 6/2003 | Thompson et al. | |
| 6,582,365 B1 | * | 6/2003 | Hines et al. | 600/300 |
| 6,585,644 B1 | | 7/2003 | Lebel et al. | |
| 6,600,952 B1 | | 7/2003 | Snell et al. | |
| 6,602,191 B1 | | 8/2003 | Quy | |
| 6,614,406 B1 | | 9/2003 | Amundson et al. | |
| 6,622,043 B1 | | 9/2003 | Kraus et al. | 607/27 |
| 6,622,050 B1 | | 9/2003 | Thompson | |
| 6,659,948 B1 | | 12/2003 | Lebel et al. | |
| 6,662,048 B1 | * | 12/2003 | Balczewski et al. | 607/21 |
| 6,675,045 B1 | | 1/2004 | Mass et al. | 607/32 |
| 6,687,546 B1 | | 2/2004 | Lebel et al. | 607/60 |
| 6,708,065 B1 | | 3/2004 | Von Arx et al. | |
| 6,809,701 B1 | | 10/2004 | Amundson et al. | |
| 2001/0027331 A1 | | 10/2001 | Thompson | |
| 2001/0047125 A1 | | 11/2001 | Quy | 600/300 |
| 2002/0013614 A1 | | 1/2002 | Thompson | |
| 2002/0065539 A1 | | 5/2002 | Von Arx et al. | 607/60 |
| 2002/0147388 A1 | | 10/2002 | Mass et al. | |
| 2003/0018369 A1 | * | 1/2003 | Thompson et al. | 607/60 |
| 2003/0028902 A1 | | 2/2003 | Cubley et al. | |
| 2003/0114897 A1 | | 6/2003 | Von Arx et al. | |
| 2003/0114898 A1 | | 6/2003 | Von Arx et al. | |
| 2003/0149459 A1 | | 8/2003 | Von Arx et al. | |
| 2004/0102815 A1 | | 5/2004 | Balczewski et al. | |
| 2004/0260363 A1 | | 12/2004 | Arx et al. | |
| 2005/0134520 A1 | | 6/2005 | Rawat et al. | |

FOREIGN PATENT DOCUMENTS

EP        1050265        11/2000

* cited by examiner

METHOD AND SYSTEM FOR IMPROVED SPECTRAL EFFICIENCY OF FAR FIELD TELEMETRY IN A MEDICAL DEVICE

CROSS-REFERENCE TO RELATED APPLICATION(S)

This application claims the benefit of U.S. Provisional Patent Application No. 60/401,966, filed on Aug. 8, 2002, under 35 U.S.C. § 119(e).

TECHNICAL FIELD

This invention relates generally to telemetry for an implantable medical device and particularly, but not by way of limitation, to telemetry using a far field transmitter.

BACKGROUND

Radio frequency (RF) interference can disrupt reception of a desired signal. To reduce the impact of interference, many governmental entities have established standards and regulations to limit the transmission bandwidth of RF transmitters having an output power in excess of a predetermined level. For example, in the United States, long range RF transmissions are regulated by the Federal Communications Commission (FCC) and in Europe, the European Telecommunications Standards Institute (ETSI) proposes standards for consideration and implementation by individual countries.

In general, the telemetry system of an implantable medical device includes a near field inductive coil. Typically, the near field telemetry system does not generate far field RF interference and thus, can operate in compliance with standards and regulations. On the other hand, near field telemetry systems do not allow long range communication between the implanted device and an external programmer.

What is needed is a long range telemetry system suitable for use with an implantable medical device that conforms to standards and regulations limiting RF interference.

SUMMARY

Radio frequency transmissions from a far field transmitter of an implantable medical device are adjusted based on a sensed temperature. To comply with regulatory requirements, guard bands of transmitter frequency spectrum are established. The bandwidth of the guard bands is adjusted based on temperature. For example, when implanted in a body, the device is subjected to a narrow range of temperatures thus allowing the guard bands to be narrowed and, therefore, a greater amount of bandwidth is available for data telemetry.

A temperature sensor controls the operation of a radio frequency transmitter in an implanted medical device. The transmitter performance, as measured by the transmitted frequency spectrum, is adjusted to comply with regulatory requirements. In one embodiment, the output power level of the transmitter is reduced for predetermined temperatures. In one embodiment, the transmission data rate is reduced for predetermined temperatures. In one embodiment, the supply voltage to the transmitter is disabled for predetermined temperatures. The transmitter is adapted for operating in one of two or more modes wherein the mode is selected based on a sensed temperature or the presence or absence of a lead.

In addition, by limiting the temperature range at which transmissions are made, the supply voltage to the transmitter can be reduced. Reducing the supply voltage to the transmitter, for example, provides increased battery life.

Temperature measuring and storing is disclosed in commonly assigned U.S. patent application Ser. No. 09/823,260, filed Mar. 3, 2001, titled IMPLANTABLE MEDICAL DEVICE WITH TEMPERATURE MEASURING AND STORING CAPABILITY, inventors Ron A. Balczewski et al., and herein incorporated by reference.

In one embodiment, wave shaping is used to improve spectral efficiency within a selected bandwidth for modulation products above a predetermined amplitude. A programmable digital to analog converter (DAC) drives a modulation input of an implanted transmitter.

This summary is intended to provide a brief overview of some of the embodiments of the present system, and is not intended in an exclusive or exhaustive sense, and the scope of the invention is to be determined by the attached claims and their equivalents.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
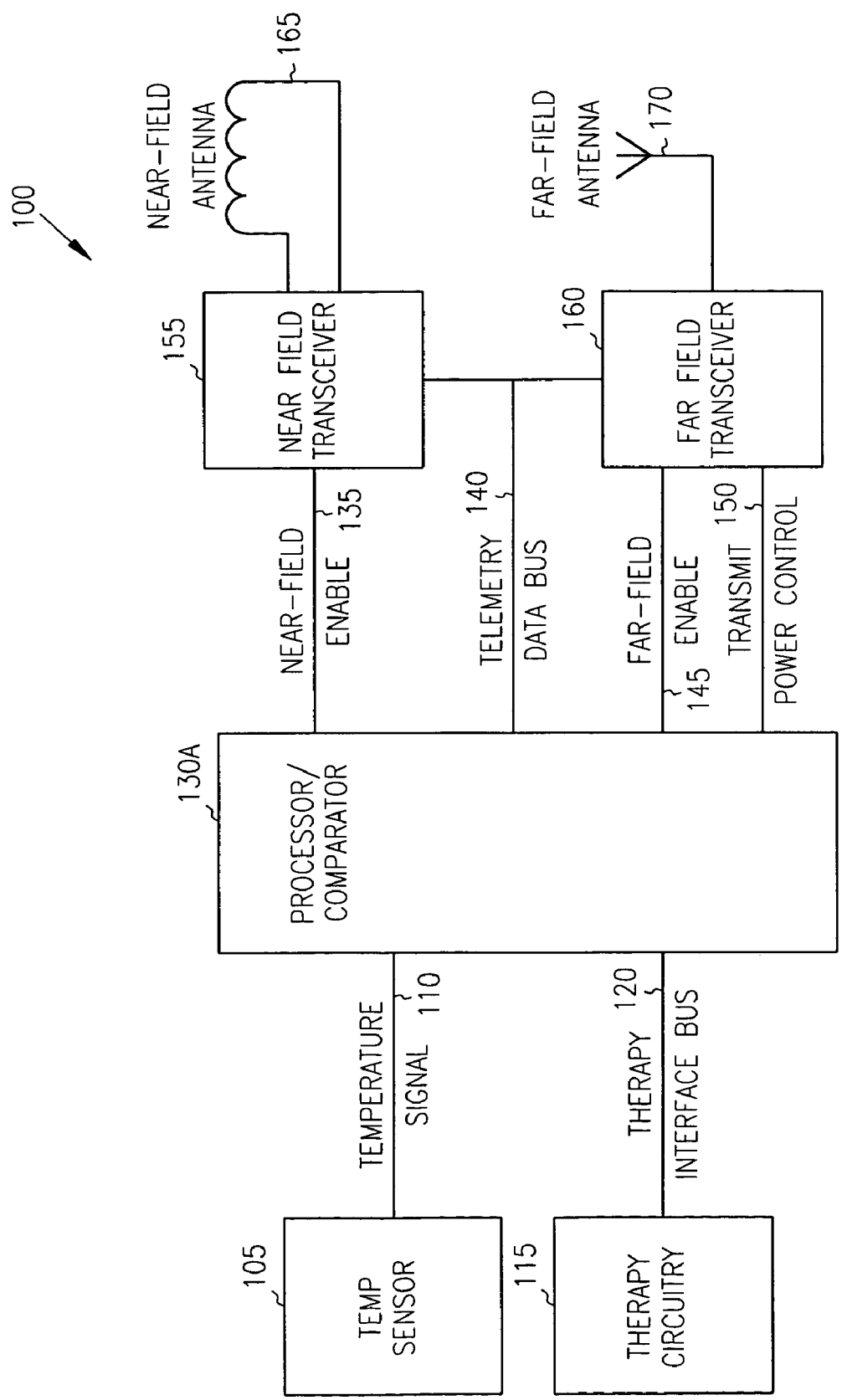
FIG. 1 illustrates a block diagram of an implanted medical device having near field and far field telemetry circuitry.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

As illustrated in FIG. 1, implanted medical device 100 includes temperature sensor 105 coupled to microcontroller, or processor, 130A, via signal line 110. Processor 130A is further coupled to therapy circuit 115, via therapy interface bus 120, and is also coupled to near field transceiver 155 and far field transceiver 160. In the figure, far field telemetry transceiver 160 includes a transmitter adapted to transmit at an output power level as determined by transmit power control 150. Near field telemetry and far field telemetry are described in commonly assigned U.S. patent application Ser. No. 10/025,183, filed Dec. 19, 2001, entitled AN IMPLANTABLE MEDICAL DEVICE WITH TWO OR MORE TELEMETRY SYSTEMS, inventors Jeffrey A. Von Arx et al, and herein incorporated by reference.

In one embodiment, temperature sensor 105 provides an analog output signal. In one embodiment, temperature sensor 105 provides a digital output signal. For example, temperature sensor 105 may include a resistive temperature device (RTD) driven by a current source, a thermistor or a thermocouple. As another example, temperature sensor 105 includes a transistor or semiconductor device, the performance of which varies with temperature.

In one embodiment, temperature sensor 105 includes a circuit or device that provides a current proportional to absolute temperature, $I_{PTAT}$. Typically, $I_{PTAT}$ is used to generate a reference voltage with a bandgap reference voltage. In addition, $I_{PTAT}$ also provides a convenient way of measuring the device temperature. In one embodiment, $I_{PTAT}$ is used to feed a variable frequency oscillator. The oscillator generates a clock signal with a frequency proportional to the current, and thus, proportional to the temperature.

Temperature sensor 105 may be incorporated into an external lead, such as for example, an intravenous lead. In one embodiment, sensor 105 is disposed internal to a housing of device 100.

In one embodiment, a sensor interface is provided to communicate temperature data from temperature sensor 105 to processor 130A. The sensor interface, may include, for example, sampling circuitry and an analog-to-digital converter. In the figure, line 110 carries the output of temperature sensor 105 to processor 130A.

Processor 130A is coupled to therapy circuit 115 by therapy interface bus 120. Therapy circuit 115 may include a pulse generator, a defibrillation circuit, a cardioverter or other therapy circuitry.

Processor 130A is coupled to near field transceiver 155 and far field transceiver 160 by telemetry data bus 140. In one embodiment, telemetry data bus 140 includes a serial data bus. The serial data bus may signal a transmit mode or sleep mode or other control signals. In one embodiment, telemetry data bus 140 includes an 8-bit bus, however, a bus with greater or fewer bits, or an analog line may also be used. Telemetry data bus 140 is adapted to communicate data between processor 130A and transceivers 155 and 160. Processor 130A is coupled to near field transceiver 155 by near field enable 135 and coupled to far field transceiver 160 by far field enable 145.

Near field transceiver 155 transmits and receives using near field antenna 165. Far field transceiver 160 transmits and receives using far field antenna 170.

In one embodiment, processor 130A is coupled to far field transceiver 160 by transmit power control 150. Transmit power control 150 provides a signal to far field transceiver 160 based on a temperature sensed by temperature sensor 105. For example, in one embodiment, when temperature sensor 105 indicates that a temperature is between a predetermined upper level and a predetermined lower level, transmit power control 150 communicates a signal to far field transceiver 160. The transmit power control signal instructs far field transceiver 160 to transmit a wireless signal at a first predetermined output level. For temperatures not between the upper and lower levels, transmit power control 150 instructs far field transceiver 160 to transmit a wireless signal at a second predetermined level.

In one embodiment, transmit power control 150 includes one or more conductors and conveys an analog signal or digital data. In one embodiment, transmit power control 150 is modulated by a DAC.

Figure 2:
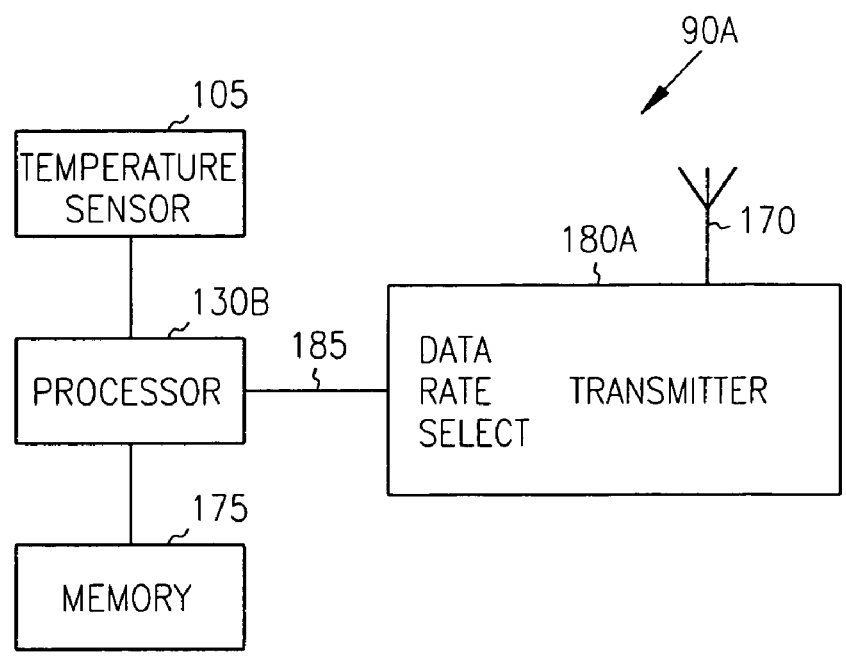
FIG. 2 illustrates a portion of an implanted medical device having a selectable transmission data rate.

FIG. 2 illustrates system 90A of an implantable medical device. Processor 130B is coupled to temperature sensor 105, memory 175 and transmitter 180A. Transmitter 180A, in one embodiment, includes a far field transmitter and transmits an RF signal using far field antenna 170. Using line 185, processor 130B provides a signal to transmitter 180A selecting the transmission data rate. Transmitter 180A transmits a far field signal at a predetermined rate as specified by processor 130B. The data transmitted by transmitter 180A may include data received from processor 130B, a therapy circuit, temperature sensor 105, or other sensors or components of the implantable medical device through electrical connections, some of which are not illustrated in the figure. In one embodiment, transmitter 180A is combined with an RF receiver.

In one embodiment, line 185 carries a digital signal. In one embodiment, line 185 carries an analog signal. Line 185 may include one or more conductors. In one embodiment, the data rate is communicated to transmitter 180A as a multiple bit digital word. In one embodiment, the available data rates are half clock speed, clock speed or twice clock speed.

In one embodiment, transmitter 180A is adapted to transmit data at one of two predetermined data rates. In one embodiment, transmitter 180A is adapted to transmit data at variable data rates.

Transmitter 180A, in one embodiment, is coupled to processor 130B by a serial data bus. Data is clocked over from processor 130B to transmitter 180A at the rate at which the data is to be transmitted.

Processor 130B is adapted to execute programming to select a data rate based on a temperature signal received from temperature sensor 105. Programming instructions or data may be stored in memory 175. In one embodiment, the programming instructions provide that for temperatures in a predetermined range, transmitter 180A transmits data at a first data rate and for temperatures not in the predetermined range, transmitter 180A transmits data at a second data rate. For example, Table 1 shows an example, wherein for temperatures below 10° C., transmitter 180A transmits at a low data rate, for temperatures above 45° C., transmitter 180A transmits at a low data rate and for temperatures between 10° C. and 45° C., transmitter 180A transmits at a high data rate. As another example, Table 2 shows one embodiment, wherein for temperatures below 10° C., transmitter 180A transmits at a low data rate, for temperatures between 10° C. and 20° C., transmitter 180A transmits at a medium data rate, for temperatures between 20° C. and 45° C., transmitter 180A transmits at a high data rate and for temperatures greater than 45° C., transmitter 180A transmits at a low data rate.

In different embodiments, temperatures other than 10° C. and 45° C. are used. For example, 20° C. and 43° C. are used in one embodiment. In general, a narrower temperature range means that less frequency spectrum is to be allocated for temperature variations, and thus, more frequency spectrum remains available for data telemetry. The lower temperature value, in one embodiment, is determined based on an estimated time for an implantable device to transition from a frozen environment to the lower temperature limit in a room temperature environment. The upper temperature value, in one embodiment, is determined based on anticipated localized heating caused by electrical activity (such as charging) of the implantable device.

TABLE 1

| Temperature X (in ° C.) | Transmission Data Rate |
|---|---|
| 45 < X | low |
| 10 < X < 45 | high |
| X < 10 | low |

TABLE 2

| Temperature X (in ° C.) | Transmission Data Rate |
|---|---|
| 45 < X | low |
| 20 < X < 45 | high |
| 10 < X < 20 | medium |
| X < 10 | low |

Figure 3:
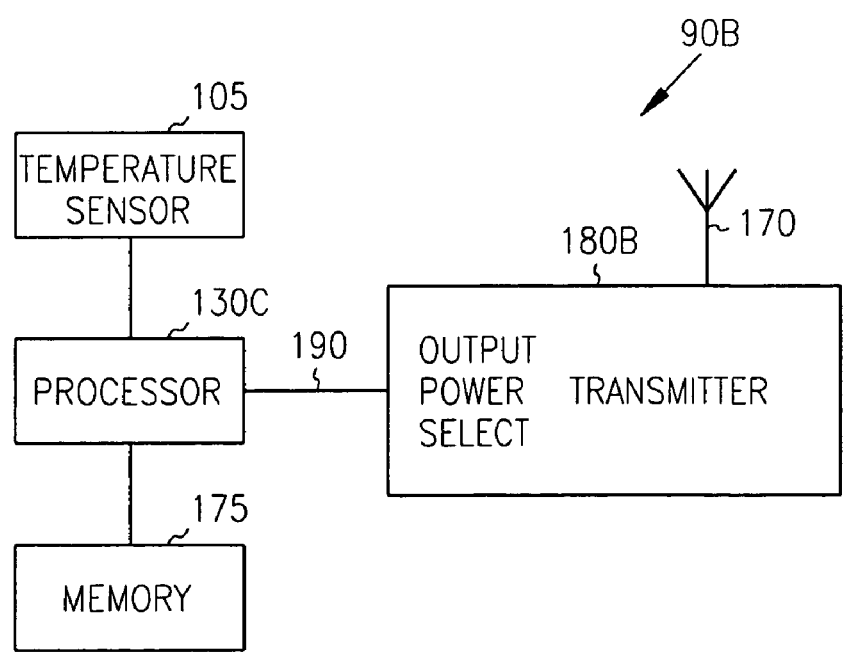
FIG. 3 illustrates a portion of an implanted medical device having a selectable transmission output power.

FIG. 3 illustrates system 90B of an implantable medical device. Processor 130C is coupled to temperature sensor 105, memory 175 and transmitter 180B. Transmitter 180B, in one embodiment, includes a far field transmitter and transmits an RF signal using far field antenna 170. Using line 190, processor 130C provides a signal to transmitter 180B selecting the transmission output power. Transmitter 180B transmits a far field signal at a predetermined output power as specified by processor 130C. The data transmitted by transmitter 180B may include data received from processor 130C, a therapy circuit, temperature sensor 105, or other sensors or components of the implantable medical device through electrical connections, some of which are not illustrated in the figure. Transmitter 180B, in one embodiment, is combined with an RF receiver.

In one embodiment, line 190 carries a digital signal. In one embodiment, line 190 carries an analog signal. Line 190 may include one or more conductors. In one embodiment, the output power is communicated to transmitter 180B as a multiple bit digital word.

In one embodiment, transmitter 180B is adapted to transmit data at one of two predetermined output power levels. In one embodiment, transmitter 180B is adapted to transmit data at variable output power levels.

Processor 130C is adapted to execute programming to select an output power based on a temperature signal received from temperature sensor 105. Programming instructions or data may be stored in memory 175. In one embodiment, the programming instructions provide that for temperatures in a predetermined range, transmitter 180B transmits data at a first output power and for temperatures not in the predetermined range, transmitter 180B transmits data at a second output power. For example, Table 3 shows one embodiment, wherein for temperatures below 10° ° C., transmitter 180B transmits at a low output power level, for temperatures above 45° C., transmitter 180B transmits at a low output power level and for temperatures between 10° C. and 45° C., transmitter 180B transmits at a high output power level. According to one embodiment, a low output power level corresponds to a signal level of −20 dBm and a high output power level corresponds to a signal level of 0 dBm (1 milliwatt). As another example, Table 4 shows one embodiment, wherein for temperatures below 10° C., transmitter 180B transmits at a low output power level, for temperatures between 10° C. and 20° C., transmitter 180B transmits at a medium output power level, for temperatures between 20° C. and 45° C., transmitter 180B transmits at a high output power level and for temperatures greater than 45° C., transmitter 180B transmits at a low output power level. According to one embodiment, a medium output power level corresponds to a signal level of −10 dBm.

TABLE 3

| Temperature X (in ° C.) | Transmission Output Power |
|---|---|
| 45 < X | low |
| 10 < X < 45 | high |
| X < 10 | low |

TABLE 4

| Temperature X (in ° C.) | Transmission Output Power |
|---|---|
| 45 < X | low |
| 20 < X < 45 | high |
| 10 < X < 20 | medium |
| X < 10 | low |

Figure 4:
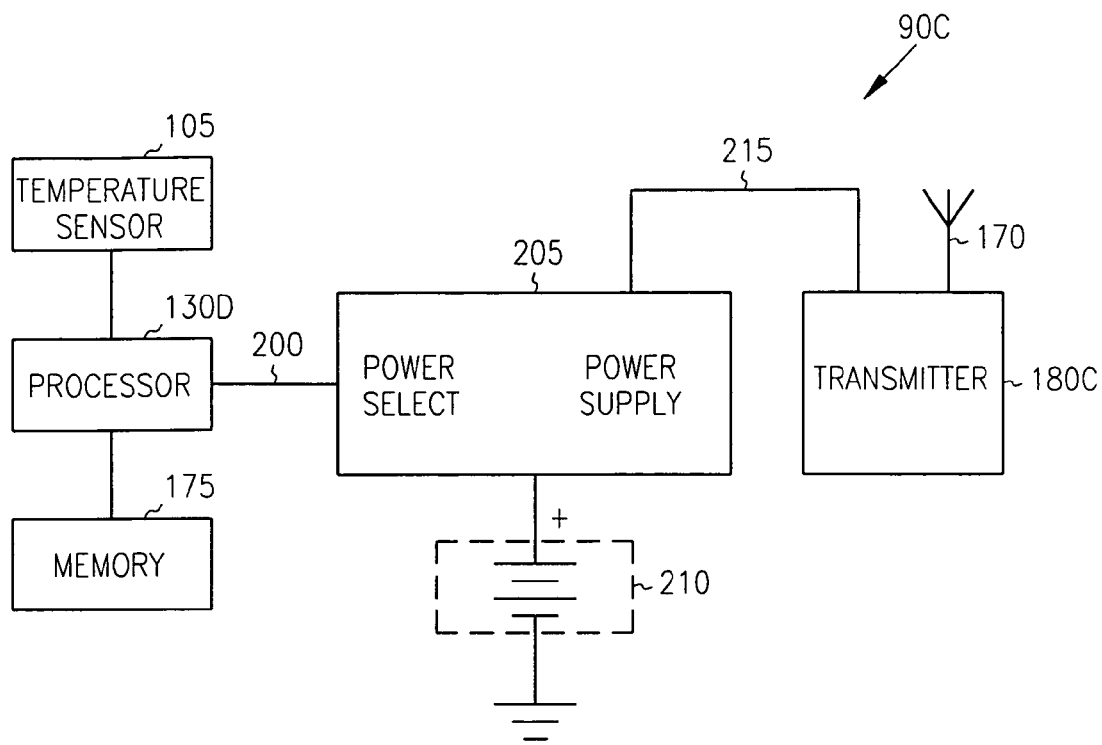
FIG. 4 illustrates a portion of an implanted medical device having a power supply with a selectable output.

FIG. 4 illustrates system 90C of an implantable medical device. Processor 130D is coupled to temperature sensor 105, memory 175 and power supply 205. Power supply 205 is further coupled to transmitter 180C via line 215. Transmitter 180C, in one embodiment, includes a far field transmitter and transmits an RF signal using far field antenna 170. Using line 200, processor 130D provides a signal to power supply 205 selecting a power supply voltage for transmitter 180C. Power supply 205 is coupled to battery 210. Transmitter 180C transmits a far field signal at a predetermined output power using a supply voltage specified by processor 130D. The data transmitted by transmitter 180C may include data received from processor 130D, a therapy circuit, temperature sensor 105, or other sensors or components of the implantable medical device through electrical connections, some of which are not illustrated in the figure. Transmitter 180C, in one embodiment, is combined with an RF receiver.

In one embodiment, line 200 carries a digital signal. In one embodiment, line 200 carries an analog signal. Line 200 may include one or more conductors. In one embodiment, the voltage supplied to transmitter 180C is communicated to power supply 205 as a multiple bit digital word. In one embodiment, power supply 205 includes a switch, controlled by processor 130D, that supplies the output voltage of battery 210 to transmitter 180C at line 215. The switch, in one embodiment, includes a transistor or other semiconductor switch.

Transmitter 180C is adapted to transmit data using a supply voltage between two predetermined levels. In one embodiment, the supply voltage is higher when the temperature is outside of a predetermined range and the supply voltage is lower when the temperature is within the predetermined range. In one embodiment, transmitter 180C is disabled for temperatures outside a predetermined range. For example, in one embodiment, the power supplied to transmitter 180C is slightly increased or removed for temperatures outside the range between 10° C. and 45° C.

Processor 130D is adapted to execute programming to operate transmitter 180C based on a temperature signal received from temperature sensor 105. Programming instructions or data may be stored in memory 175. In one embodiment, the programming instructions provide that for temperatures in a predetermined range, transmitter 180C transmits data using a first supply voltage and for temperatures not in the predetermined range, transmitter 180C is disabled. For example, Table 5 shows one embodiment, wherein for temperatures below 10° C., transmitter 180C is not powered, for temperatures above 45° C., transmitter 180C is not powered and for temperatures between 10° C. and 45° C., transmitter 180C transmits using a regulated supply voltage. As another example, Table 6 shows one embodiment, wherein for temperatures below 10° C., transmitter 180C is not powered, for temperatures between 10° C. and 20° C., transmitter 180C transmits using a slightly increased, regulated, supply voltage, for temperatures between 20° C. and 45° C., transmitter 180C transmits using a reduced, regulated supply voltage and for temperatures greater than 45° C., transmitter 180C is not powered. In one embodiment, an increased supply voltage is nominally 2.4 volts and a reduced supply voltage is 2.2 volts. Battery longevity is improved by adjusting the transmitter power supply voltage.

In one embodiment, the supply voltage to transmitter 180C remains relatively constant and for predetermined temperatures, transmitter 180C is disabled. Disabling transmitter 180C, in one embodiment, includes removing the supplied power. In one embodiment, disabling transmitter 180C includes actuating a switch based on a control signal.

TABLE 5

| Temperature X (in ° C.) | Transmitter Supply Voltage |
|---|---|
| 45 < X | off |
| 10 < X < 45 | regulated |
| X < 10 | off |

TABLE 6

| Temperature X (in ° C.) | Transmitter Supply Voltage |
|---|---|
| 45 < X | off |
| 20 < X < 45 | regulated, reduced |
| 10 < X < 20 | regulated, increased |
| X < 10 | off |

Figure 5:
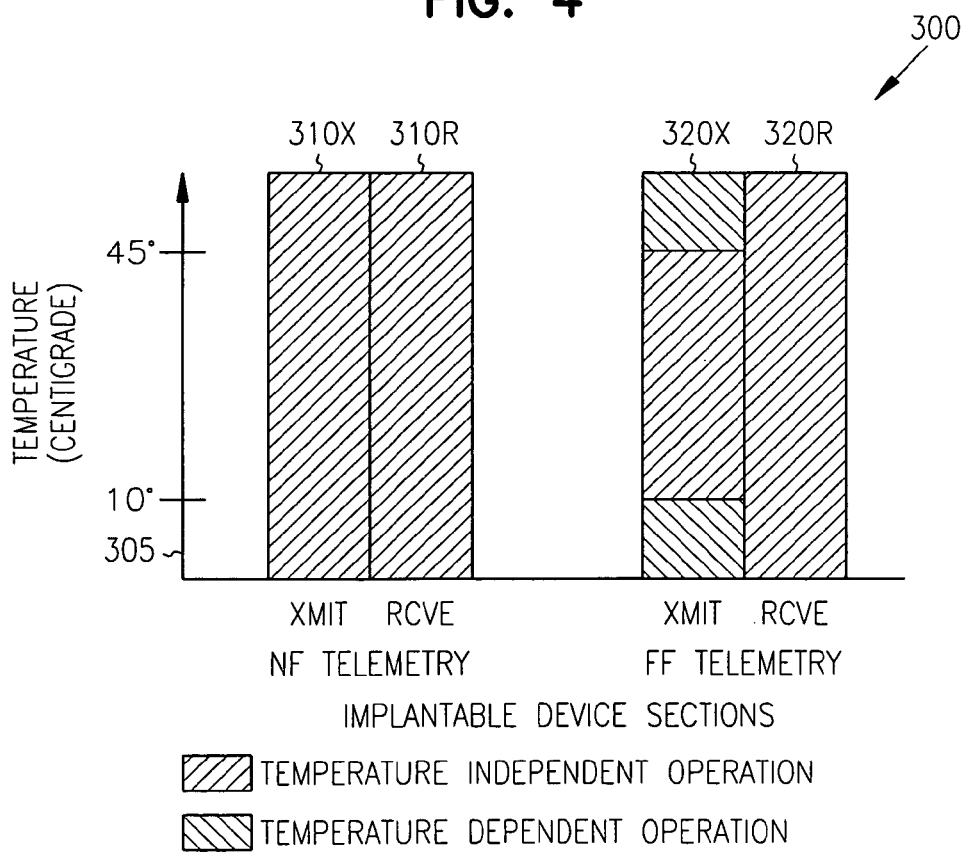
FIG. 5 graphically illustrates operational modes as a function of temperature.

FIG. 5 provides graphical illustration 300 depicting telemetry functions of an implantable device based on temperature. In one embodiment, the implantable medical device includes a near field transceiver and a far field transceiver.

The near field transmitter, as shown at column 310X, and near field receiver, as shown at column 310R, and the far field receiver, as shown at column 320R, operate without temperature compensation. Performance of near field transmitter, near field receiver and far field receiver is not processor controlled based on a sensed temperature. The performance of the far field transmitter, on the other hand, is processor controlled based on a sensed temperature. In the figure, for temperatures below 10° C. or for temperatures above 45° C., the bandwidth of the far field transmitter is attenuated and for temperatures between 10° C. and 45° C., the far field transmitter is operated without bandwidth attenuation.

Figure 6A:
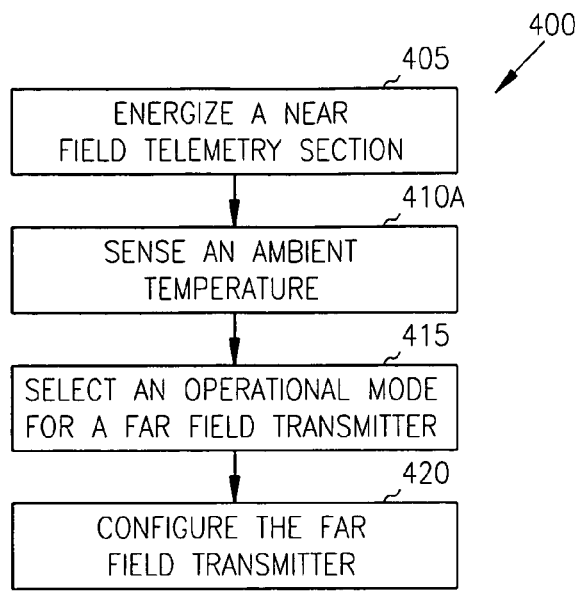
FIG. 6A illustrates a portion of a flow chart in accordance with one embodiment of the present subject matter.

FIG. 6A illustrates a flow chart of method 400 performed by one embodiment of the present subject matter. In the figure, the near field telemetry system is energized at 405. The near field telemetry system, in one embodiment, is continuously available. At 410A, an ambient temperature is sensed. If the device is implanted in a healthy human body, the ambient temperature sensed will be approximately body temperature. If, the device is not yet implanted, the ambient temperature sensed may be greater or less than body temperature.

At 415, the present subject matter selects an operational mode for the far field transmitter. The operational mode, for example but not by way of limitation, may provide a reduced bandwidth by limiting the data rate, limiting the transmitter output power, or by reducing or removing the supply voltage to the transmitter. A processor, or other circuitry of the implantable device, selects an operation mode, and at 420, signals the far field transmitter accordingly.

In one embodiment, the temperature is periodically checked at a frequency of once every 10 second, however greater or lower sampling frequencies may also be used.

Figure 7:
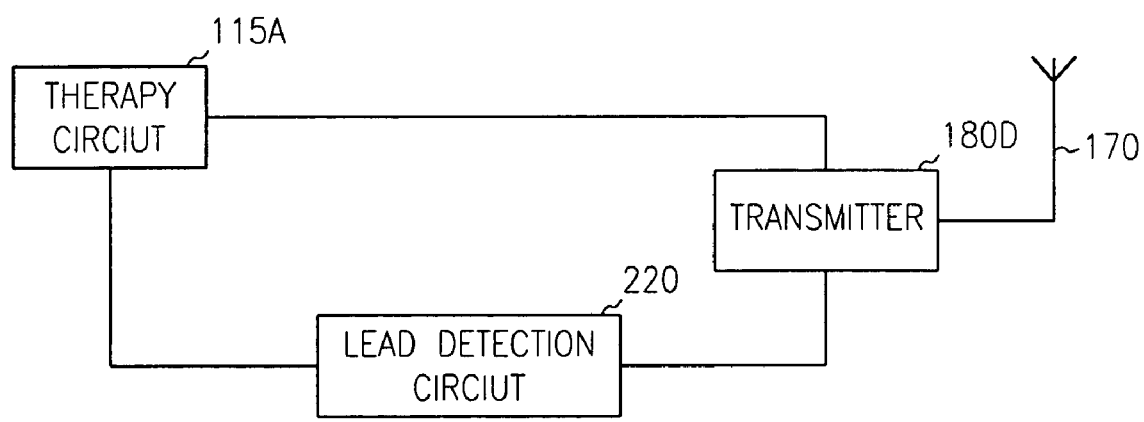
FIG. 7 illustrates a block diagram of an embodiment having a lead detection circuit.

In one embodiment, a circuit determines if a lead is connected to the implanted device. In one embodiment, circuitry or programming determines an impedance, or measures another parameter characteristic of the presence of a lead. FIG. 7 illustrates lead detection circuit 220 coupled to therapy circuit 115A and coupled to far field transmitter 180D. Lead detection circuit 220 provides a signal to far field transmitter 180D indicative of the presence, or absence, of a lead coupled to therapy circuit 115A. In one embodiment, if a lead is connected to the implanted device, it is assumed that the device has been implanted and the transmitted data rate can be raised to a nominal rate or the transmitter output power is raised to a nominal value. If a lead is not connected, then the data is transmitted at a reduced data rate or the transmitter output power is reduced. In one embodiment, the transition from a low data rate to a high data rate, or from a low output power level to a high output power level, is delayed by a predetermined period of time following detection of a lead. For example, in one embodiment, the transmitted data rate is increased thirty minutes after detecting that a lead has been attached to the implantable device. In one embodiment, the selection of a data rate or output power is determined based on lead detection and is independent of temperature.

Figure 6B:
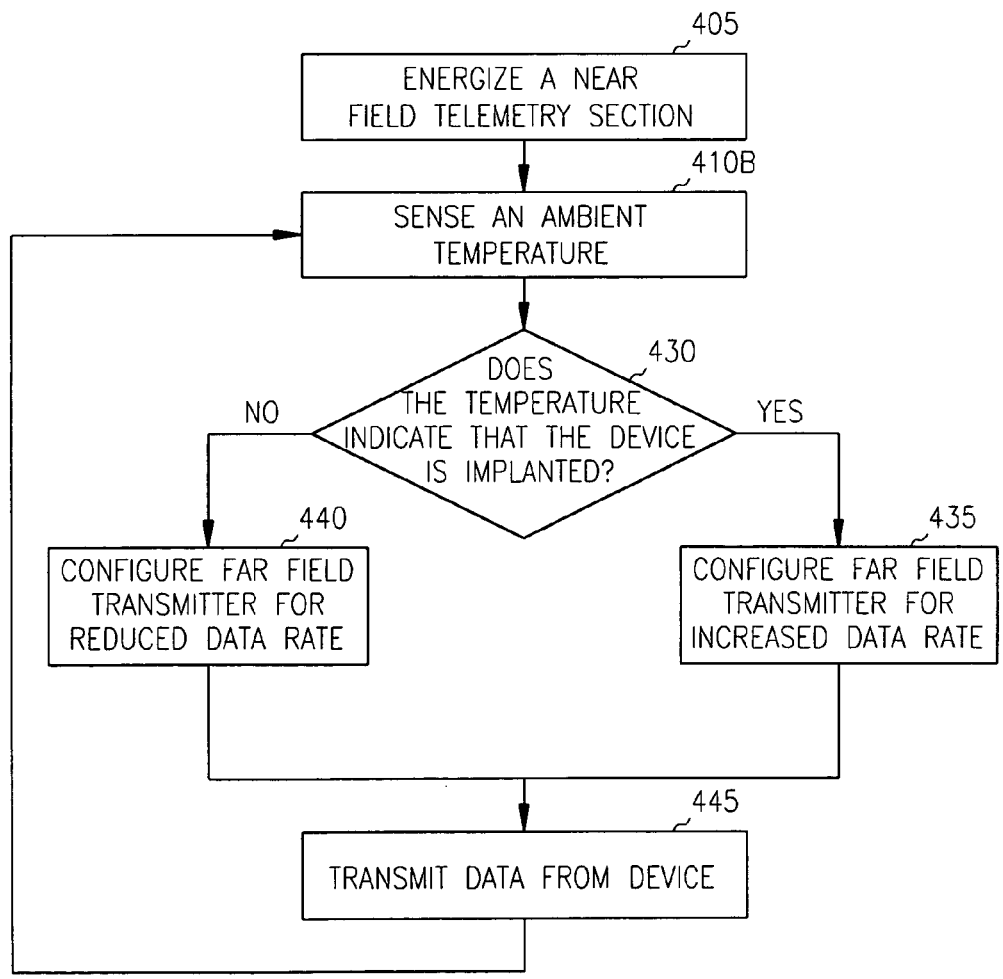
FIG. 6B illustrates a portion of a flow chart in accordance with one embodiment of the present subject matter.

In FIG. 6B, an ambient temperature is sensed at 410B. At 430, a query is presented to determine if the sensed temperature indicates that the implantable device is implanted in a body. In one embodiment, the query of 430 includes comparison of the sensed temperature with stored data. For example, if the sensed temperature is between 10° C. and 45° C., one embodiment provides that the device is implanted.

If the sensed temperature indicates that the implantable device is within the predetermined temperature range, then, at 435, the far field transmitter is configured for transmitting at an increased data rate. If, on the other hand, the temperature indicates that the device is not implanted, then at 440, the far field transmitter is configured for transmitting at a reduced data rate. In one embodiment, the transmitter output power is adjusted based on the sensed temperature. Adjusting the data rate is one method for reducing bandwidth and, as described herein, other methods are also contemplated, including, for example, adjusting the output power level.

At 445, data is transmitted using the far field transmitter configured according to 435 or 440. The method returns to 4101B for further checking of the ambient temperature. In this manner, the configuration of the far field transmitter is continuously updated based on the sensed temperature.

Figure 8A:
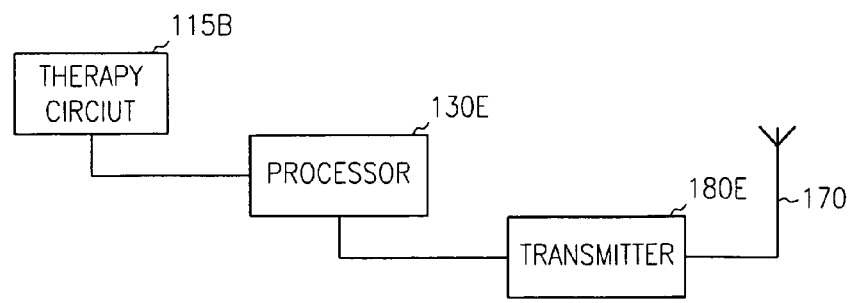
FIGS. 8A, 8B and 8C illustrate block diagrams of implantable devices adapted for wave shaping.

In one embodiment, wave shaping is used to condense the spectral content of the communicated signal, thereby allowing an increased rate of data transmission. Wave shaping includes smoothing of abrupt transmissions in the time domain to reduce bandwidth when viewed in the frequency domain. FIG. 8A illustrates one embodiment of wave shaping. In the figure, therapy circuit 115B is coupled to far field transmitter 180E via processor 130E. In one embodiment, processor 130E provides a signal to far field transmitter 180E corresponding to the data to be transmitted. In one embodiment, processor 130E provides a signal to far field transmitter 180E corresponding to an output power level at which the data is to be transmitted. In one embodiment, processor 130E provides signal processing to adapt the signal provided to far field transmitter 180E according to bandwidth availability. Wave shaping may be conducted based on amplitude modulation, frequency modulation or phase modulation. In one embodiment, the amplitude of the transmitted digital data is modulated with an envelope. The envelope, in various embodiments, includes a sine wave, a Haversine wave or other smooth transition signal. In one embodiment, the medical device applies wave shaping to transmitted data for all temperatures.

In one embodiment, the present subject matter is adapted to communicate using the SRD k-sub band having a frequency between 869.7 and 870.0 MHz. According to one standard, for far field transmissions in this band, radiated power is to be –36 dBm outside of the 300 kHz band. Table 7 illustrates allocation of the 300 kHz band according to one exemplary embodiment.

TABLE 7

| Bandwidth | Description |
| --- | --- |
| 122 kHz | modulation products above –36 dBm |
| 135 kHz | transceiver tolerance |
| 33 kHz | drift due to temperature (10–45° C.) |
| 10 kHz | guard bands |
| 300 kHz | total |

Waveshaping is used in one embodiment to satisfy the bandwidth allocation of 122 kHz for modulation products above –36 dBm. In one embodiment, waveshaping is accomplished by coupling the digital modulation input of the far field transmitter to the output of a filter, as illustrated schematically in FIG. 8B. In one embodiment, filter 230 includes a low pass filter, however other filters may also be used. In one embodiment, the filter includes a DAC which receives a digital signal and generates an analog output signal which is used to modulate the transmitter. In one embodiment, the output of a programmable DAC is coupled to the modulation input. The programmable DAC can be reconfigured to meet design objectives. FIG. 8C illustrates one embodiment wherein processor 130G is coupled to far field transmitter 180G via a series combination of DAC 235 and filter 240. The programmable DAC may include a programmable current DAC or programmable voltage DAC.

In amplitude shift keying (ASK) transmission two transmit power levels are used to represent a logic 0 and a logic 1. In one embodiment, a current driven into a modulation input pin of a transceiver controls the transmit power output. For example, a current of 10 µA drive represents a logic 0 and 450 µA current drive represents a logic 1. The spectral content of the transmission can be reduced by providing a smooth transition between the two logic levels.

Figure 9A:
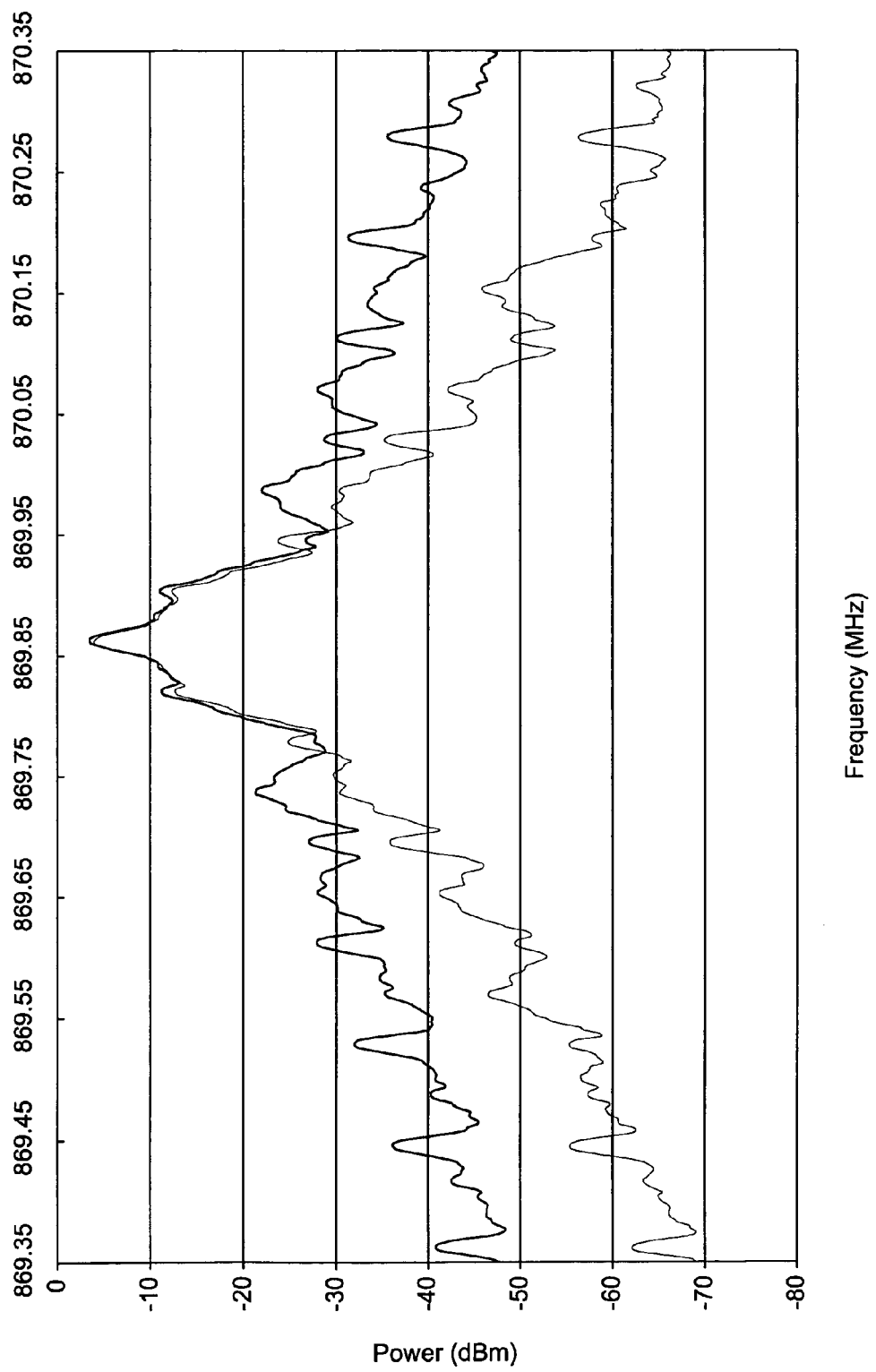
FIGS. 9A, 9B, 9C, 9D, 9E and 9F illustrate frequency response diagrams for various embodiments.

FIG. 9A graphically illustrates one embodiment of the reduction in modulation products above –36 dBm because of waveshaping of the modulation input. In the example illustrated, the data rate is 83.333 kbps, an 8-bit DAC was used for waveshaping, and full modulation depth. As shown, at the –36 dBm limit, the bandwidth of the modulation products for the non-waveshaped signal is 760 kHz and for the waveshaped signal is 337.5 kHz. In this example, waveshaping reduces the spectral bandwidth by over 50%.

In one embodiment, waveshaping parameters are selected to yield a desired bandwidth reduction. For example, the shape of the waveform can be selected to reduce spectral distribution. In one embodiment, a Haversine waveform shape is selected. In one embodiment, a waveform approximating a Haversine is selected. In one embodiment, a waveshape having symmetrical rising and falling edges is used to maintain bit timing and avoid introduction of edge jitter.

As another example, in one embodiment, a wave shaped Haversine is approximated by discrete steps of a DAC and the number of bit intervals is selected to achieve a desired bandwidth. The number of bit intervals that waveshaping is divided into affects how well a Haversine can be duplicated. In one embodiment, 12 intervals yields the desired data rate and maintains uniform interval spacing. The number of bit intervals can be greater or less than 12.

Figure 9B:
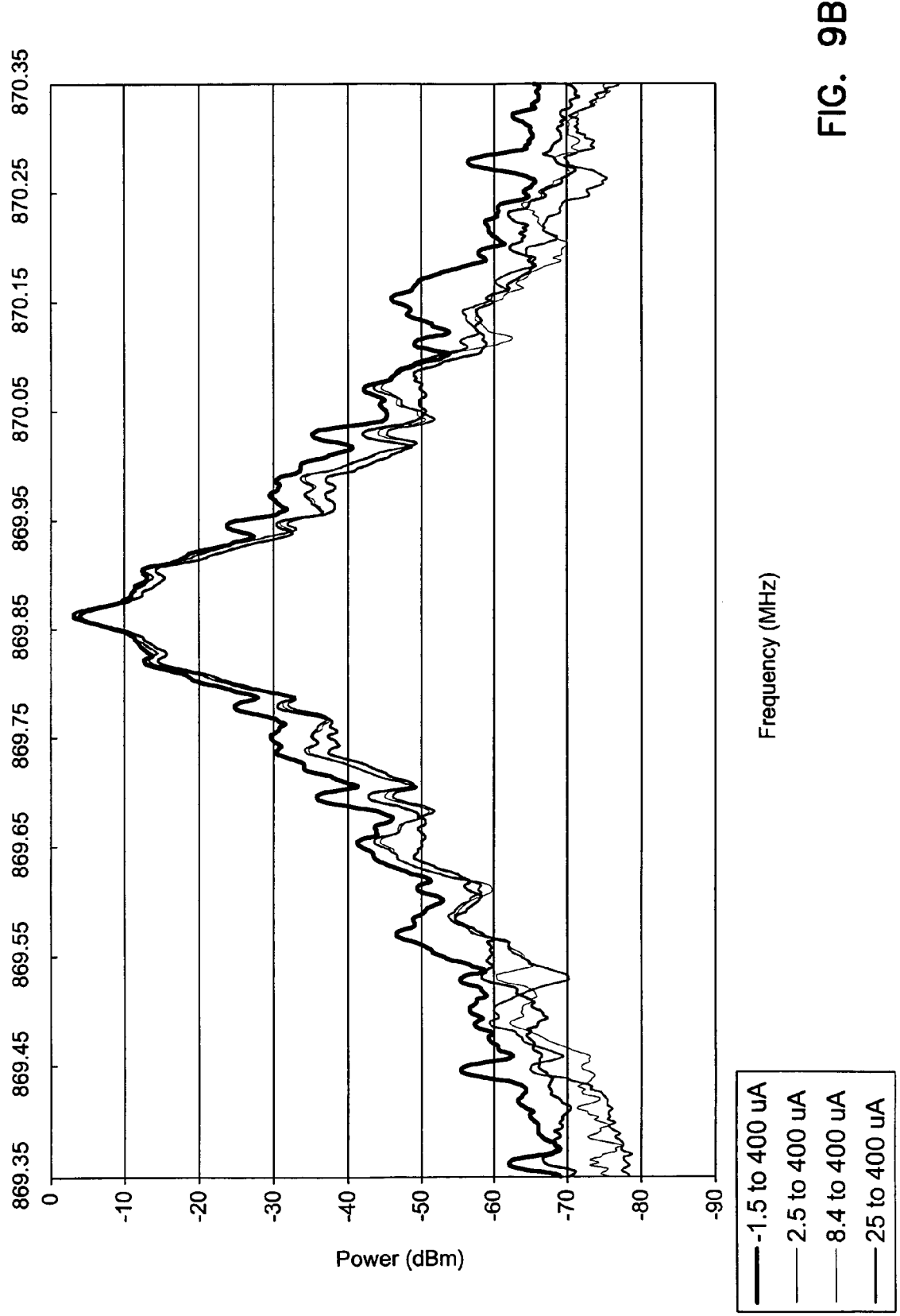

As another example, in one embodiment, the modulation depth is selected to achieve a desired bandwidth. Decreasing the modulation depth decreases the modulation products above –36 dBm by narrowing the main lobe and suppressing sidebands of the transmitted signal. With further reductions in the modulation depth, either by increasing the power level for the logic 0 or by decreasing the power level for the logic 1 or by a combination of both, the noise margins of the received signal decreases. With reduced noise margins, the signal to noise ratio of the receiver is decreased, thus reducing the maximum range of the system. FIG. 9B illustrates modulation products with changing modulation depth. Data presented in Table 8 shows that decreasing the modulation depth from full range to something less than full range decreases the bandwidth of modulation products above –36 dBm. The table also shows the reduction in the difference between the transmitted power for logic 0 and logic 1 with continued reduction in bandwidth.

TABLE 8

| Bandwidth of Modulation Products above –36 dBm | Modulation Depth |
| --- | --- |
| 337.5 kHz | 61.9 dB |
| 260.0 kHz | 48.2 dB |
| 260.0 kHz | 35.4 dB |
| 185.0 kHz | 23.6 dB |

Figure 9C:
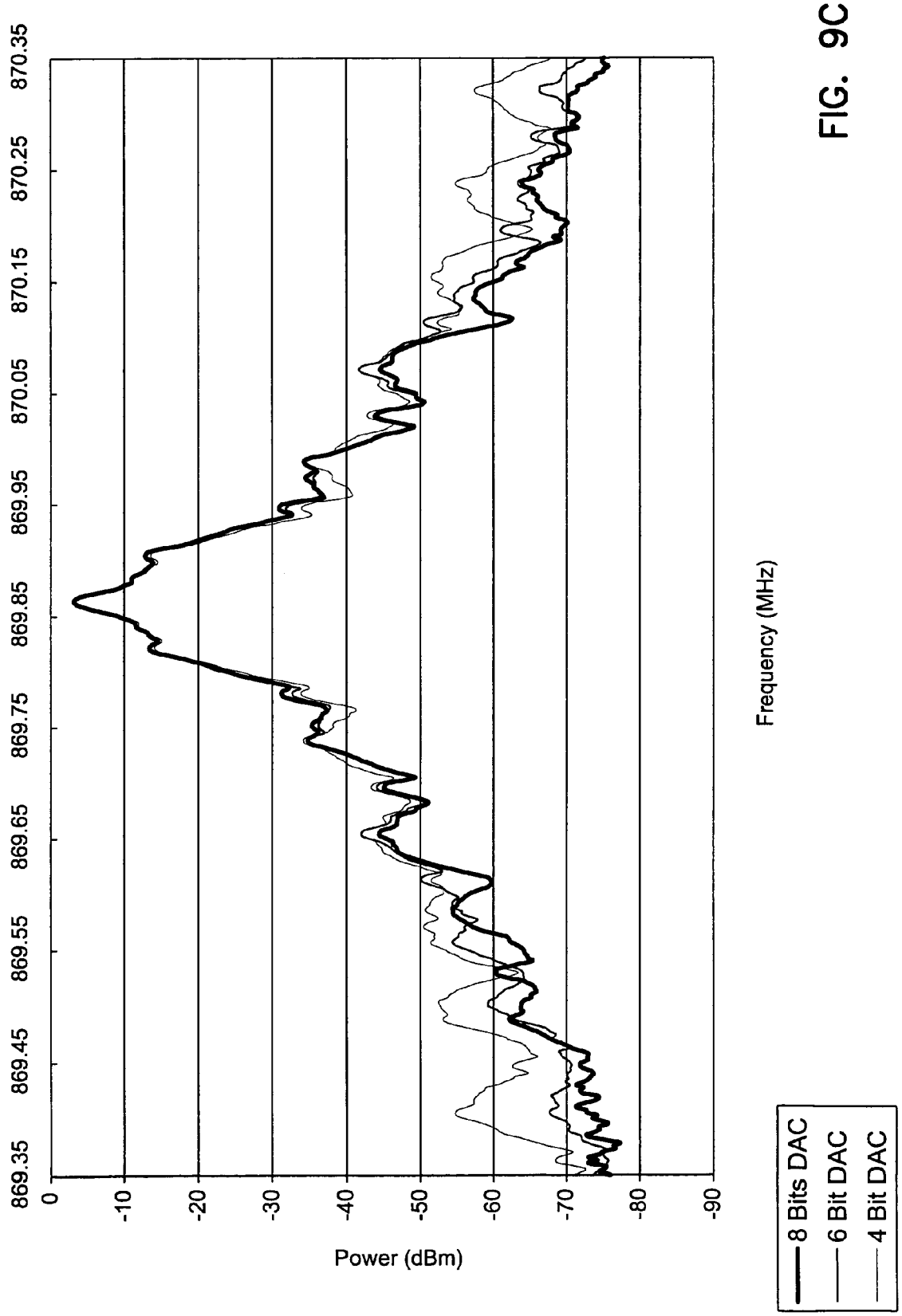

As another example, in one embodiment, the number of bits to modulate transmit power is selected to achieve a desired bandwidth. The resolution of the waveshaping steps is controlled by the number of DAC bits. FIG. 9C graphically illustrates the effects of varying the number of DAC bits. As shown in the figure, reducing the number of DAC bits to four bits has little effect on the bandwidth of modulation products above –36 dBm. The power in the side lobes increases upon reduction in the number of DAC bits but does not exceed the –36 dBm limit.

Figure 9D:
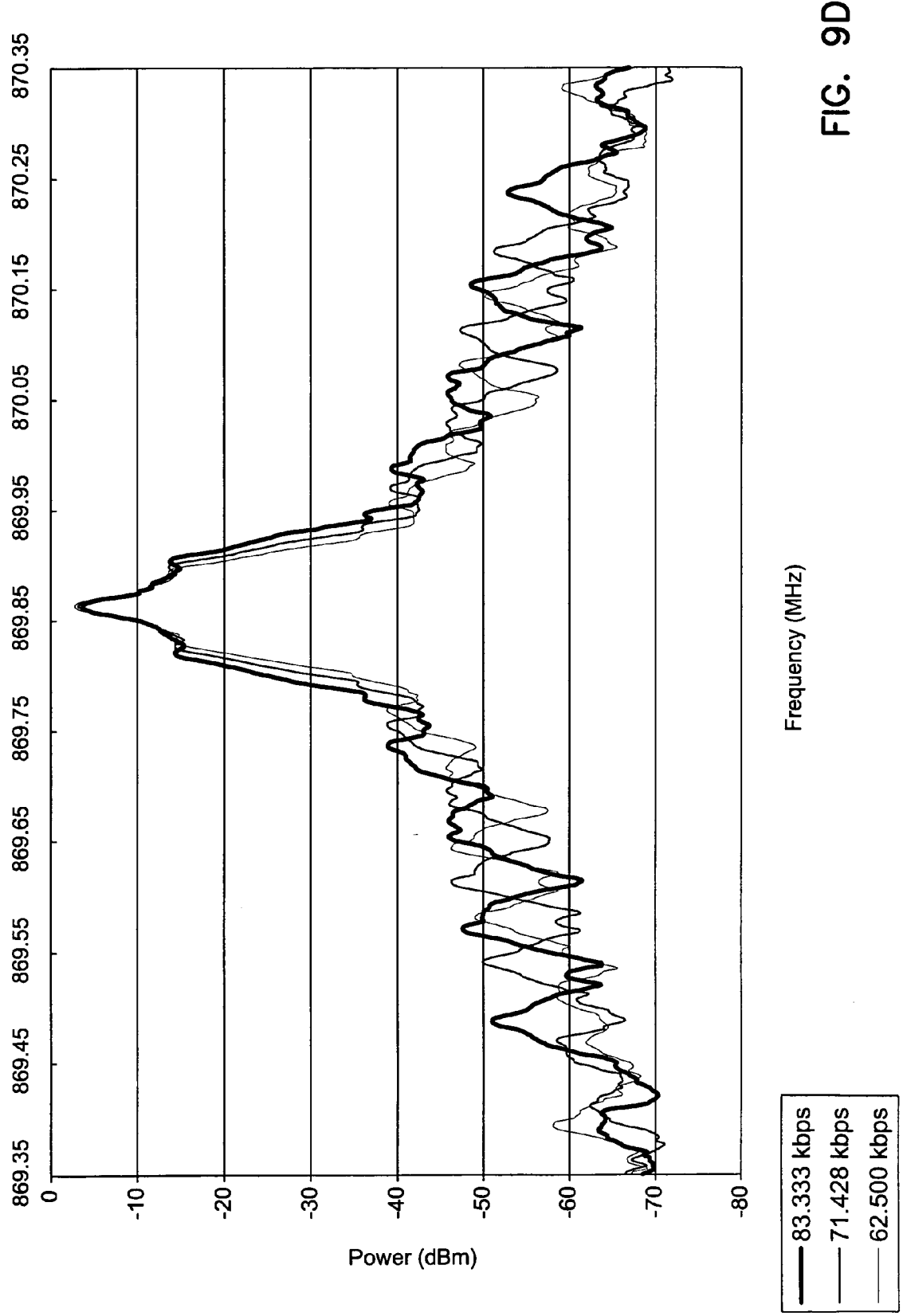

As another example, in one embodiment, the data rate is selected to achieve a desired bandwidth. For ASK transmissions, the data rate effects the spread of the transmit spectrum. In general, the higher the data rate, the greater the spread of the spectrum. FIG. 9D graphically illustrates modulation products as a function of data rate.

Figure 9E:
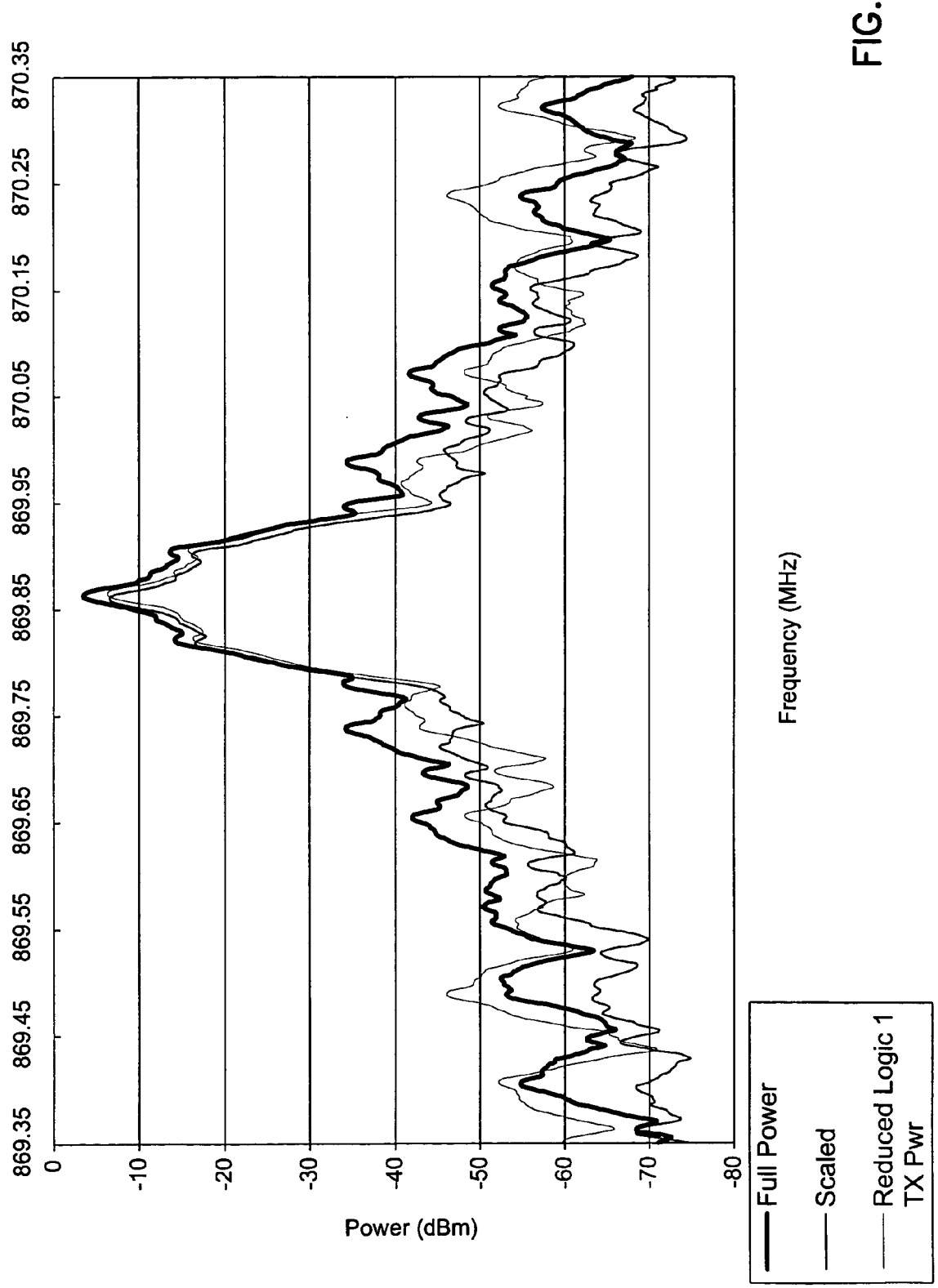

As another example, in one embodiment, the peak transmit power is selected to achieve a desired bandwidth. By reducing the logic 1 transmit power the modulation waveform can be lowered. If the logic 0 current level is maintained, then reducing the logic 1 transmit power also reduces the modulation depth. If both logic 1 and logic 0 transmit powers are scaled down, modulation depth can be maintained. In either case, reducing the peak transmit power will result in a decrease in the maximum range. FIG. 9E graphically illustrates modulation products as a function of peak transmit power. As shown in the figure, reducing the peak transmit power decreases the bandwidth of the modulation products above −36 dBm.

Figure 9F:
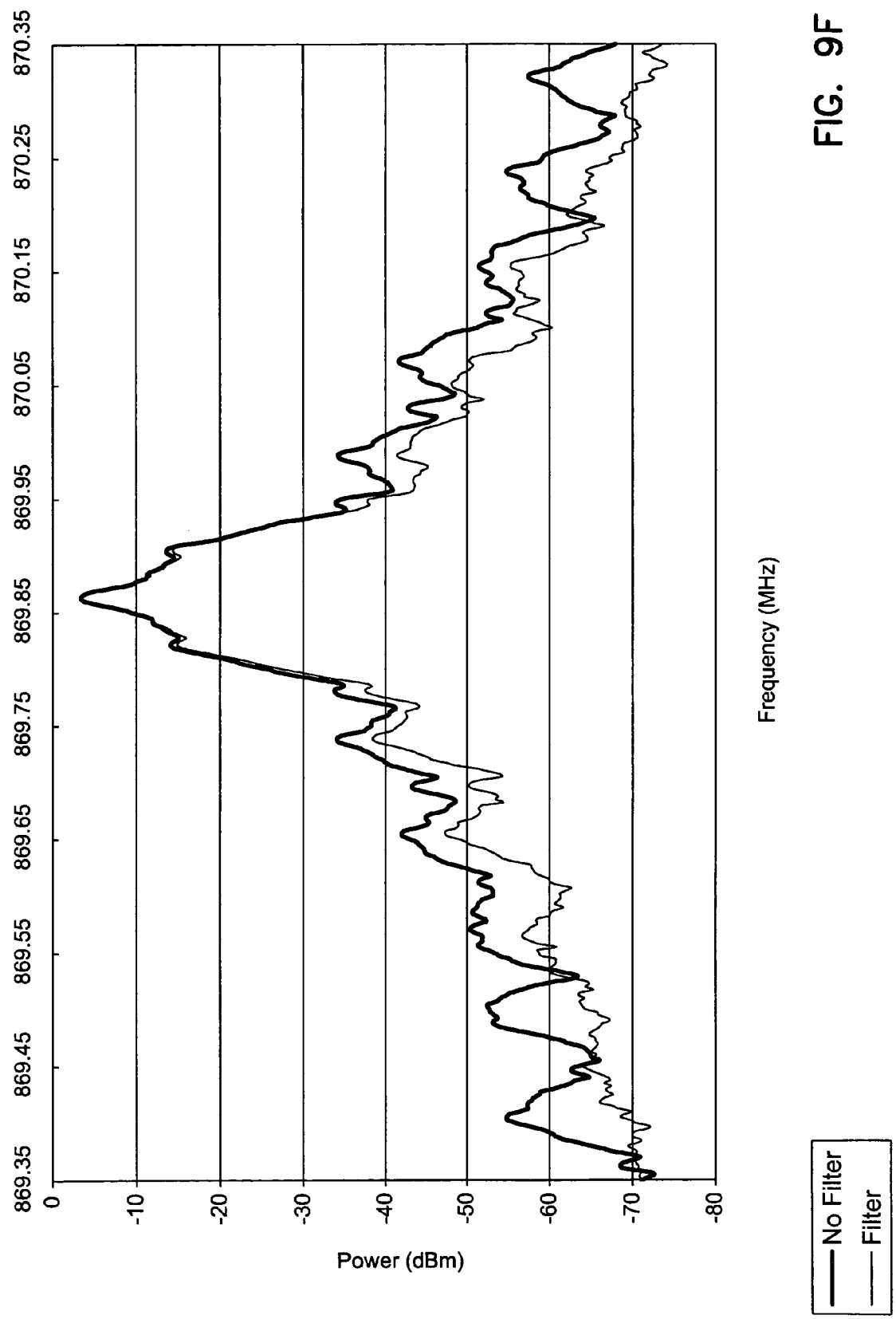

As another example, in one embodiment, the output of the DAC is filtered to achieve a desired bandwidth. A single pole RC low pass filter on the output of the current DAC can smooth the transitions between intervals. FIG. 9F graphically illustrates the changes in the bandwidth after filtering the DAC output. As shown in the figure, the filtered waveform exhibits a reduction in the bandwidth of the modulation products above −36 dBm mainly from suppressing the side lobe power.

ALTERNATIVE EMBODIMENTS

Variations of the above embodiments are also contemplated. For example, in one embodiment, the present subject matter reduces the amount of frequency spectrum allocated to temperature drift, thereby increasing the bandwidth available for data transmission. For instance, temperature compensation permits a far field data transmission rate to be increased from 50 kilobytes per second (KBPS) to 69 KBPS.

For telemetry at temperatures outside of the narrow range of body temperatures, or other predetermined range, the bandwidth of the transmitter is reduced. In one embodiment, the bandwidth is reduced by lowering the output power of the transmitter, by for example, 20 dB. A 20 dB reduction in output power is approximately that which is encountered due to tissue losses when the device is implanted in a body. In one embodiment, the transmitter operates at a reduced data rate for temperatures outside the specified range of temperatures. In one embodiment, the far field transmitter is powered off or operated at a reduced power supply voltage for temperatures outside the specified range of temperatures. In one embodiment, near field telemetry is available at all temperatures.

In one embodiment, the far field transmitter includes a surface acoustic wave (SAW) oscillator (or resonator) based transmitter. The SAW transmitter operates, for example in the range of 100's of MHz. According to one governmental regulatory specification, short range device (SRD) transmitters are tested over a temperature range of 0° C. to 55° C. In this range, a SAW transmitter may vary by 60 kHz. Over a range of temperatures from 20° C. to 45° C., a SAW transmitter may vary by 25 kHz. When used in a temperature controlled environment, such as when implanted, the 35 kHz bandwidth difference can be used to increase the data transmission rate.

In one embodiment, the far field transmitter includes a crystal based circuit, such as, for example, a phase-locked loop (PLL) up-converted crystal controlled transmitter.

In one embodiment, the far field transmitter is fabricated using bipolar device technology. For example, with bipolar transistors, the threshold voltage, base to emitter ($V_{BE}$) typically varies linearly with temperature. Over a temperature range of 0° C. to 55° C., the $V_{BE}$ for each transistor varies approximately 100 millivolts (mV) and for one exemplary multiple transistor transmitter circuit, the variation is approximately 200 mV. Transistor performance variations as a function of temperature are expressed as a temperature coefficient. The same transmitter circuit, over a narrower temperature range of 20° C. to 45° C., exhibits variation of $V_{BE}$ of 53 mV. Thus, the reduced $V_{BE}$ variation over the narrower temperature range allows operating the transmitter with a power supply voltage reduced by approximately 140 mV.

In one embodiment, the present subject matter allows a reduction in the supply voltage provided to the far field transceiver. For example, one embodiment allows reducing the supply voltage from 2.4 volts to 2.2 volts.

In one embodiment, the output power level of the transmitter is controlled by a current source. A bias current is adjusted using a trimmer. In one embodiment, the output power level is programmable. In one example, a register stores a power level as a multiple bit word.

In one embodiment, a combination of data rate, output power level and supply voltage is used to determine transmission bandwidth.

In one embodiment, after determining the temperature, the present subject matter adjusts and maintains a particular transmission bandwidth for a predetermined window of time.

In one embodiment, the frequency of sampling the temperature changes as a function of temperature. For example, at extreme temperatures, a first sampling frequency is used and at temperatures in a predetermined range, a second sampling frequency is used, where the second sampling rate is slower than the first sampling rate.

In one embodiment, the output transmission power level is continuously variable. In one embodiment, the output transmission power level is selected from two or more available discrete power levels.

In one embodiment, the variable data rate is adjusted for discrete temperature bands.

In one embodiment, the processor provides error correction in sensed temperatures. Programming and data for the processor may be stored in memory accessible to the processor.

In one embodiment, a comparator provides an output signal based on a temperature or based on the presence or absence of a lead. The output signal from the comparator is coupled to the transmitter. The comparator, in one embodiment, includes an analog comparator. A reference voltage supplied to the comparator is used for comparison. The comparator, in one embodiment, includes a processor and a comparison is made between the sensed temperature and data stored in a memory.

CONCLUSION

The above description is intended to be illustrative, and not restrictive. Many other embodiments will be apparent to those of skill in the art upon reviewing the above description.

What is claimed is:

1. A system comprising:
an implantable temperature sensor adapted to provide an output signal based on a sensed temperature;
an implantable comparator coupled to the sensor and adapted to generate a control signal based on the output signal; and
an implantable wireless transmitter coupled to the implantable comparator and adapted to modulate a transmission bandwidth based on the control signal.

2. The system of claim 1 wherein the implantable comparator includes a processor.

3. The system of claim 1 further including an implantable therapy circuit coupled to the implantable wireless transmitter.

4. The system of claim 1 wherein the transmitter includes a surface acoustic wave (SAW) resonator.

5. The system of claim 1 wherein the wireless transmitter is adapted to transmit at two or more output power levels.

6. The system of claim 1 wherein the wireless transmitter is adapted to transmit at two or more data rates.

7. The system of claim 1 wherein the implantable wireless transmitter is adapted to be disabled based on the control signal.

8. The system of claim 1 further including a digital to analog converter (DAC) coupled to an implantable processor and adapted to provide the control signal.

9. An apparatus comprising:
a far field transmitter coupled to an implantable medical device, the transmitter having two or more selectable transmission frequency spectrums and a frequency spectrum select means;
a temperature sensor having an output signal based on a temperature; and
a controller coupled to the frequency spectrum select means and coupled to the output signal, the controller adapted to select one transmission frequency spectrum of the two or more selectable transmission frequency spectrums based on the output signal.

10. The apparatus of claim 9 further including a telemetry circuit coupled to the implantable medical device.

11. The apparatus of claim 9 wherein the controller is adapted to adjust a voltage level.

12. The apparatus of claim 9 wherein the controller is adapted to adjust a current level.

13. The apparatus of claim 9 wherein the controller is adapted to adjust a transmission data rate.

14. The apparatus of claim 9 wherein the controller is adapted to adjust a transmission output power level.

15. The apparatus of claim 9 wherein the controller is adapted to selectively enable the far field transmitter.

16. The apparatus of claim 9 wherein the controller is adapted to selectively energize the far field transmitter.

17. A method comprising:
sensing a temperature at an implantable device;
comparing the sensed temperature with a first temperature; and
disabling a far field transmitter of the implantable device if the sensed temperature is greater than the first temperature.

18. The method of claim 17 further including:
comparing the sensed temperature with a second temperature; and
disabling the far field transmitter if the sensed temperature is less than the second temperature.

19. The method of claim 17 wherein disabling includes removing a supply voltage.

20. A method comprising:
sensing a temperature at an implantable device;
comparing the sensed temperature with a first temperature; and
selecting a reduced output power level of a far field transmitter of the implantable device if the sensed temperature is above the first temperature.

21. The method of claim 20 further including:
comparing the sensed temperature with a second temperature; and
selecting the reduced output power level if the sensed temperature is below the second temperature.

22. The method of claim 21 further including transmitting data at an increased output power level if the sensed temperature is between the first temperature and the second temperature.

23. The method of claim 20 wherein selecting the reduced output power level includes disabling the far field transmitter.

24. A method comprising:
sensing a temperature at an implantable device;
comparing the sensed temperature with a first temperature; and
selecting a reduced telemetry data rate of a far field transmitter of the implantable device if the sensed temperature is above the first temperature.

25. The method of claim 24 further including:
comparing the sensed temperature with a second temperature; and
selecting the reduced telemetry data rate if the sensed temperature is below the second temperature.

26. The method of claim 25 further including transmitting data at an increased telemetry data rate if the sensed temperature is between the first temperature and the second temperature.

27. An apparatus comprising:
therapy delivery means adapted for implanting in a body;
sensing means adapted to provide a sense signal based on a temperature;
processor means coupled to the therapy means;
first telemetry means coupled to the processor and adapted to communicate using far field transmissions, the first telemetry means having a control input; and
wherein the control input receives a control signal based on the sense signal.

28. The apparatus of claim 27 further including a second telemetry means coupled to the processor and adapted to communicate using near field transmissions.

29. The apparatus of claim 27 wherein the control input is coupled to a transmitter output power control means, the transmitter output power control means selecting a transmitter output power of the first telemetry means based on the control signal.

30. The apparatus of claim 27 wherein the control input is coupled to a data rate control means, the data rate control means selecting a data transmission rate of the first telemetry means based on the control signal.

31. The apparatus of claim 27 wherein the control input is coupled to a transmitter disable means, the transmitter disable means selectively disabling the first telemetry means based on the control signal.

32. An apparatus comprising:
a lead detection circuit having a detection output;
an implantable transmitter having two or more modes of operation; and a mode selection circuit coupled to the implantable transmitter and adapted to provide a mode selection signal based on the detection output.

33. The apparatus of claim 32 wherein the mode selection circuit includes a comparator coupled to the lead detection circuit.

34. The apparatus of claim 33 wherein the comparator includes an analog comparator.

35. The apparatus of claim 32 wherein the mode selection circuit includes a processor coupled to the lead detection circuit.

36. The apparatus of claim 32 wherein the implantable transmitter is adapted to transmit a signal having a first bandwidth if a lead is detected and adapted to transmit a signal having a second bandwidth if the lead is not detected, wherein the first bandwidth is greater than the second bandwidth.

37. The apparatus of claim 32 wherein the implantable transmitter has a first mode corresponding to a first data rate and a second mode corresponding to a second data rate.

38. The apparatus of claim 32 wherein the implantable transmitter has a first mode corresponding to a first output power level and a second mode corresponding to a second output power level.

39. The apparatus of claim 32 wherein the implantable transmitter has a first mode corresponding to enabled and a second mode corresponding to disabled.

40. A system comprising:
an implantable therapy circuit;
a processor coupled to the therapy circuit and having a signal output;
a filter having a filter input coupled to the signal output and having a filter output; and
an implantable wireless transmitter having a modulation input coupled to the filter output and wherein an output power of the wireless transmitter is modulated as a function of the modulation input.

41. The system of claim 40 wherein the filter output provides a wave shaped signal.

42. The system of claim 40 further including a digital to analog converter (DAC) having a DAC input coupled to the signal output and a DAC output coupled to the filter input.

43. The system of claim 40 wherein the implantable wireless transmitter is adapted to provide amplitude shift key (ASK) modulation.

44. A system comprising:
an implantable therapy circuit;
a processor coupled to the therapy circuit and having a signal output;
a digital to analog converter having a digital input coupled to the signal output and having an analog output; and
an implantable wireless transmitter having a modulation input coupled to the analog output and wherein an output power of the wireless transmitter is modulated as a function of the modulation input.

45. The system of claim 44 wherein the analog output provides a wave shaped signal.

46. The system of claim 45 wherein the wave shaped signal approximates a Haversine wave.

47. A method comprising:
receiving a signal from an implanted therapy circuit;
processing the signal to provide a modulation input signal;
adjusting a far field transmitter power output based on the modulation input signal; and
wirelessly transmitting data based on the signal.

48. The method of claim 47 wherein processing includes filtering.

49. The method of claim 47 wherein processing includes low pass filtering.

50. The method of claim 47 wherein processing includes converting the signal to analog format.

51. The method of claim 47 wherein the signal includes digital data and wherein processing includes converting four bit digital data to an analog signal.

52. The method of claim 47 wherein processing includes applying a Haversine wave shaping function.

* * * * *

UNITED STATES PATENT AND TRADEMARK OFFICE
CERTIFICATE OF CORRECTION

| | | |
|---|---|---|
| PATENT NO. | : 7,069,086 B2 | Page 1 of 1 |
| APPLICATION NO. | : 10/269905 | |
| DATED | : June 27, 2006 | |
| INVENTOR(S) | : Von Arx | |

It is certified that error appears in the above-identified patent and that said Letters Patent is hereby corrected as shown below:

On Title Page Item (56), under "Foreign Patent Documents", in column 2, line 1, after "1/1986" insert -- G01K 1/02 --.

On Sheet 5 of 12, in Fig. 7 (Block - 115A), line 2, delete "CIRCIUT" and insert -- CIRCUIT --, therefor.

On Sheet 5 of 12, in Fig. 7 (Block - 220), line 2, delete "CIRCIUT" and insert -- CIRCUIT --, therefor.

On Sheet 6 of 12, in Fig. 8A (Block - 115B), line 2, delete "CIRCIUT" and insert -- CIRCUIT --, therefor.

Figure 8B:
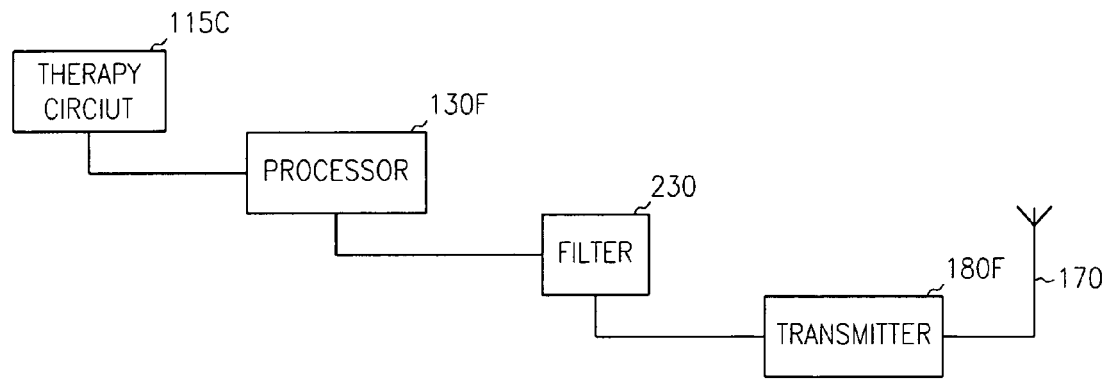
Figure 8C:
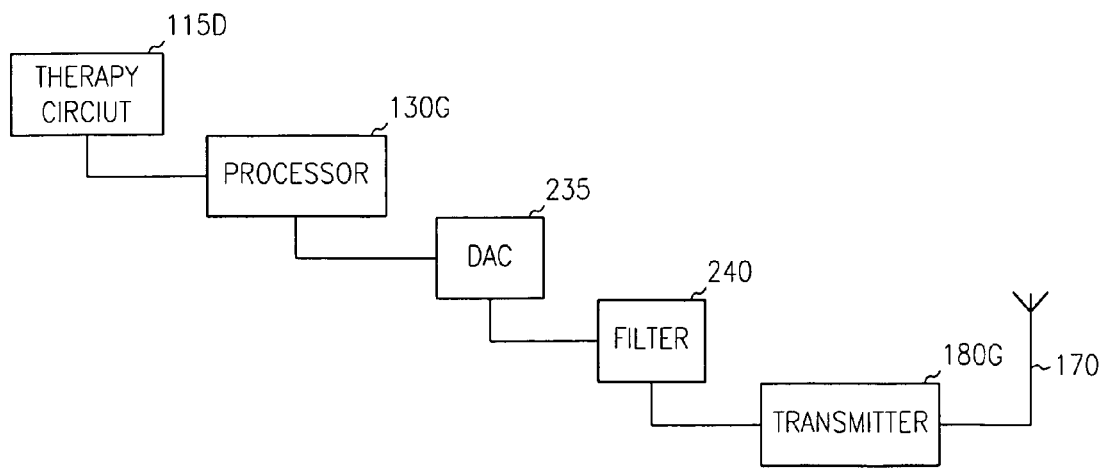

On Sheet 6 of 12, in Fig. 8B (Block -115C), line 2, delete "CIRCIUT" and insert -- CIRCUIT --, therefor.

On Sheet 6 of 12, in Fig. 8C (Block - 115D), line 2, delete "CIRCIUT" and insert -- CIRCUIT --, therefor.

Signed and Sealed this

Seventh Day of November, 2006

JON W. DUDAS
*Director of the United States Patent and Trademark Office*